US011554253B2

(12) United States Patent
Scheremet et al.

(10) Patent No.: US 11,554,253 B2
(45) Date of Patent: Jan. 17, 2023

(54) UNITARY STRAIN-RELIEVING INTRAVENOUS (IV) ANCHOR SYSTEM

(71) Applicant: FastTrack Medical Solutions LLC, Eden Prairie, MN (US)

(72) Inventors: William Scheremet, Hinkley, MN (US); Steven J. Brinkman, Eden Prairie, MN (US); Kim A. Jacobsen, Minneapolis, MN (US)

(73) Assignee: FASTTRACK MEDICAL SOLUTIONS LLC, Eden Prairie, MN (US)

( * ) Notice: Subject to any disclaimer, the term of this patent is extended or adjusted under 35 U.S.C. 154(b) by 888 days.

(21) Appl. No.: 16/276,259

(22) Filed: Feb. 14, 2019

(65) Prior Publication Data

US 2019/0247624 A1 Aug. 15, 2019

Related U.S. Application Data

(63) Continuation of application No. 14/942,614, filed on Nov. 16, 2015, now abandoned, which is a continuation of application No. 13/184,218, filed on Jul. 15, 2011, now abandoned.

(60) Provisional application No. 61/365,351, filed on Jul. 18, 2010.

(51) Int. Cl.
*A61M 25/02* (2006.01)
*A61M 5/158* (2006.01)

(52) U.S. Cl.
CPC ............ *A61M 25/02* (2013.01); *A61M 5/158* (2013.01); *A61M 2005/1586* (2013.01); *A61M 2025/026* (2013.01); *A61M 2025/0246* (2013.01)

(58) Field of Classification Search
CPC .................. A61M 25/02; A61M 5/158; A61M 2005/1586; A61M 2025/0246; A61M 2025/026
See application file for complete search history.

(56) References Cited

U.S. PATENT DOCUMENTS

| 4,669,458 A * | 6/1987 | Abraham | A61M 25/02 |
| | | | 128/846 |
| 5,645,855 A * | 7/1997 | Lorenz | A61L 15/585 |
| | | | 602/54 |
| 2003/0225377 A1* | 12/2003 | Hancock | A61M 25/02 |
| | | | 128/DIG. 6 |

(Continued)

*Primary Examiner* — Laura A Bouchelle
*Assistant Examiner* — John A Doubrava
(74) *Attorney, Agent, or Firm* — Craige Thompson; Thompson Patent Law; Timothy D. Snowden

(57) ABSTRACT

A system for strain relieving intravenous (IV) assembly includes a dressing and an anchor portion for use with the dressing. In various embodiments, the dressing may cover an injection site into a portion of a patient's body for an intravenous (IV) assembly that provides fluid communication between the injection site and a fluid reservoir remote from the injection site through a flexible tube. In an illustrative example, the anchor portion may include a first member and a second member. The first member may be secured, for example, to the dressing and may, in some examples, wrap around the tubing so as to resist axial movement of the tubing relative to the dressing. The second member may be secured to the dressing and may wrap around the tubing and a portion of the patient's body so as to resist radial movement of the tubing relative to the body.

22 Claims, 7 Drawing Sheets

(56) References Cited

U.S. PATENT DOCUMENTS

2010/0022962 A1\* 1/2010 Bierman ............... A61M 25/02
604/180
2010/0294286 A1\* 11/2010 Bellamy ............... A61M 25/02
128/887

\* cited by examiner

UNITARY STRAIN-RELIEVING INTRAVENOUS (IV) ANCHOR SYSTEM

CROSS-REFERENCE TO RELATED APPLICATIONS

This application is a Continuation and claims the benefits of the U.S. application Ser. No. 14/942,614, titled "Unitary Strain-Relieving Intravenous (IV) Anchor System," filed by Scheremet, et al., on Nov. 16, 2015, which is a Continuation and claims the benefit of U.S. application Ser. 13/184,218 titled "Unitary Strain-Relieving Intravenous (IV) Anchor System," filed by Scheremet, et al., on Jul. 15, 2011.

This application incorporates the entire contents of the foregoing application(s) herein by reference.

TECHNICAL FIELD

Various embodiments relate generally to providing strain relief to intravenous (IV) lines.

BACKGROUND

In intravenous (IV) therapy, liquid substances are administered directly into a vein. The term "intravenous" generally means "within a vein." Compared with other routes of administration, the intravenous route is probably the fastest way to deliver liquids throughout a body. Some medications, blood transfusions, and parenteral nutrition can only be administered intravenously.

SUMMARY

Certain embodiments of an IV anchor may achieve one or more advantages. For example, some embodiments may protect an IV injection site by providing strain relief to an IV injection site. In an illustrative example, certain embodiments may provide a breathable transparent window for monitoring of a junction that connects the catheter-and-hub assembly to a saline cap, IV tubing extension set, or full IV tubing. In some implementations, the IV junction and the injection site on the patient's body may be substantially protected from contamination by an exemplary dressing. In some examples, the dressing may be coated with an adhesive (e.g., hydrogel) mixed with an anti-microbial substance. Various examples may facilitate organization of the components of an IV line relative to each other and/or relative to other tubes or cords connected to a patient.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 1:
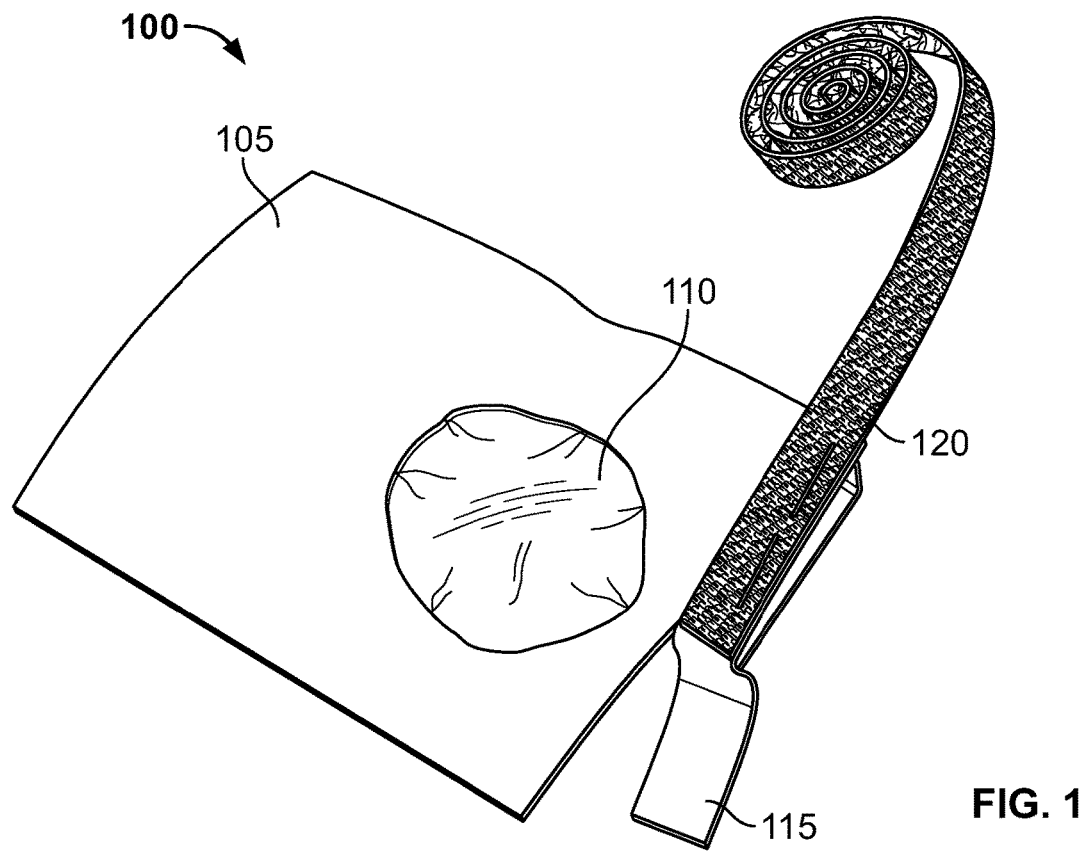
FIG. 1 depicts a a perspective view of an exemplary intravenous (IV) anchor system.

FIG. 1 depicts a perspective view of an exemplary intravenous (IV) anchor system. In the depicted example, an IV anchor system 100 is configured as a unitary device that, for example, may substantially protect an IV injection site from contamination. Some embodiments may provide substantial protection from injury to the patient and/or disruption of the IV assembly by strain relieving an IV connection assembly, or "IV line," connected to a cathether-and-hub assembly and to the injection site. Such strain relief may resist substantial axial and/or radial force components applied to the IV line (e.g., during transfer of a trauma patient from an ambulance or helicopter upon arrival at a hospital).

By way of example, and not limitation, the IV tubing assembly that connects to the catheter-and-hub assembly may include a saline cap, IV tubing extension set, and/or full length IV tubing.

The anchor system 100 is a unitary dressing apparatus formed from a first sheet of material 105, a second sheet of material 115 connected to the first sheet of material 105, and a fastening device 120 connected to the second sheet of material 115. The first sheet of material 105 includes a window 110 to allow viewing of the injection site and junction where the catheter-and-hub assembly connects with an IV connection assembly. The window 110 may be formed of plastic.

The first sheet of material 105 may include an adhesive for retaining the catheter-and-hub assembly against a body. A second sheet of material 115 may include an adhesive for retaining the tubing at a certain position relative to the catheter-and-hub assembly. The adhesive of the first and second sheets of material may be the same or different, and the adhesive of either or both of the first and second sheets of material may contain an antimicrobial substance. The first and second sheets of material 105, 115 are substantially rectangular in shape. In some embodiments, either or both of the sheets of material 105, 115 may be made of fabric alone or in combination with other materials (e.g., plastic). The fastening device 120 may include a hook and loop fastener for releasably securing to itself or to another part of the anchor after being wrapped around a portion (e.g., limb, torso) of the patient's body.

Figure 2:
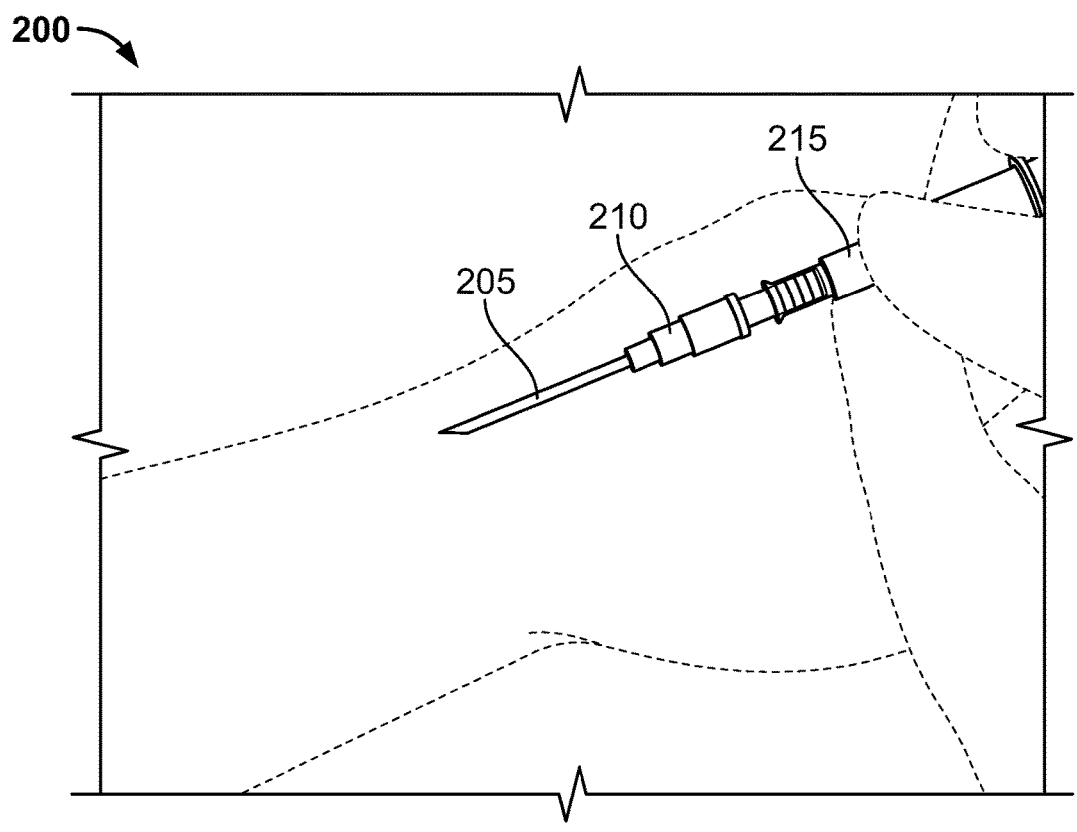
FIGS. 2, 3A and 3B depict perspective views of components of an exemplary IV line for administering IV therapy.

FIGS. 2 and 3 depict perspective views of components of an exemplary IV line for administering IV therapy. FIG. 2 depicts a perspective view of an exemplary access device for administering IV therapy. The access device 200 includes a stylet 205 inside a catheter (not shown), a connecting hub 210, and a flash chamber 215. The flash chamber and the needle may be one-piece. The flash chamber may allow observation of blood flow as an indication that the stylet has been inserted into the vein. When a care giver withdraws the stylet from the catheter, the stylet may be locked within the flash chamber to prevent accidental puncture of the care giver.

Figure 3A:
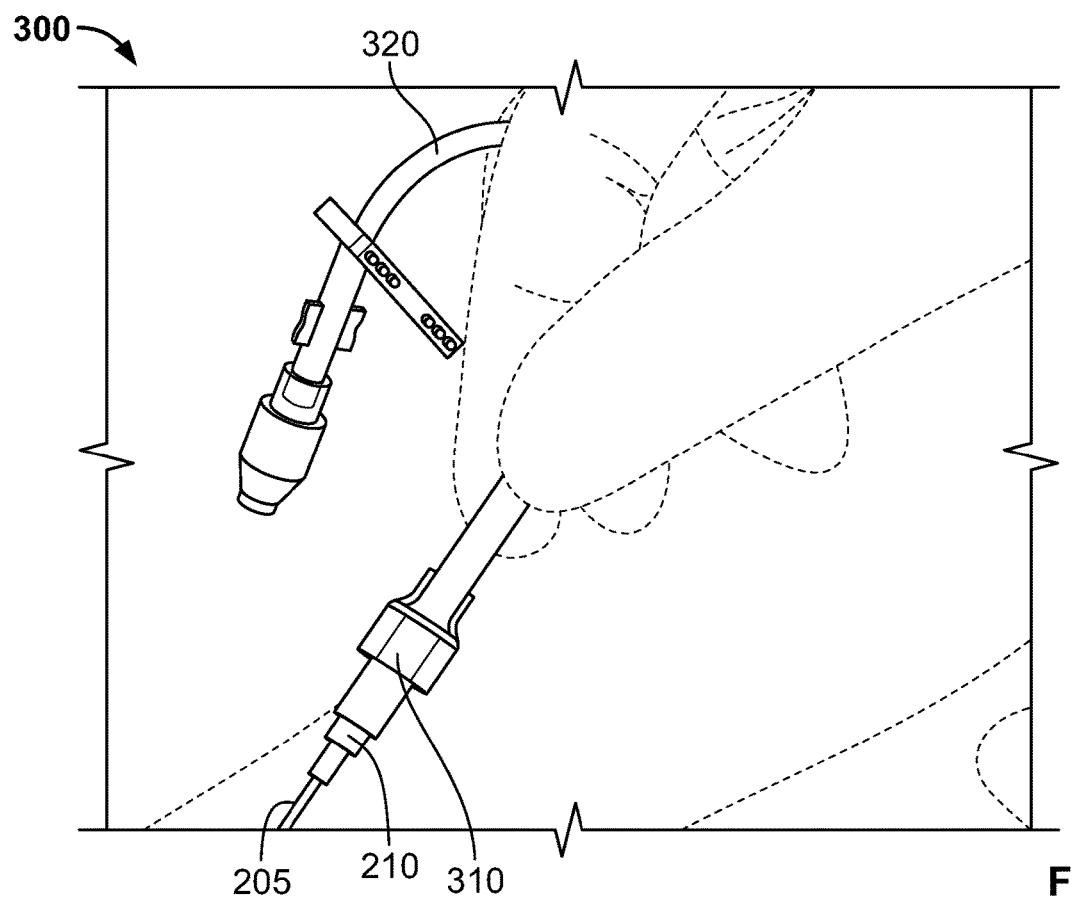
Figure 3B:
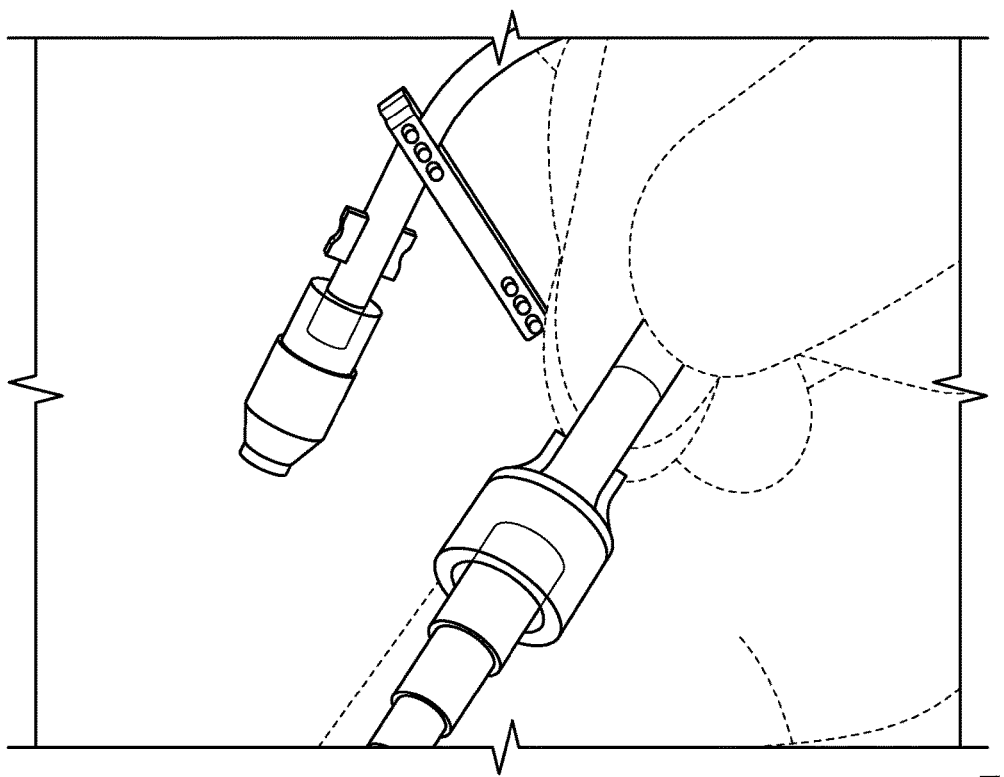

FIGS. 3A and 3B depict a perspective view of an exemplary IV line with tubing connected to the catheter-and-hub assembly of the access device of FIG. 2. The IV line 300 includes the catheter 205 and the hub 210 of the access device 200 and tubing 320. The flash chamber 215 may be removed after successful introduction of the stylet 205 into the vein of the body and replaced by tubing 320 to establish the IV line 300. When the tubing 320 is connected with the catheter-and-hub assembly 205, 210, a junction 310 is formed between the tubing 320 and the hub 210.

Figure 4:
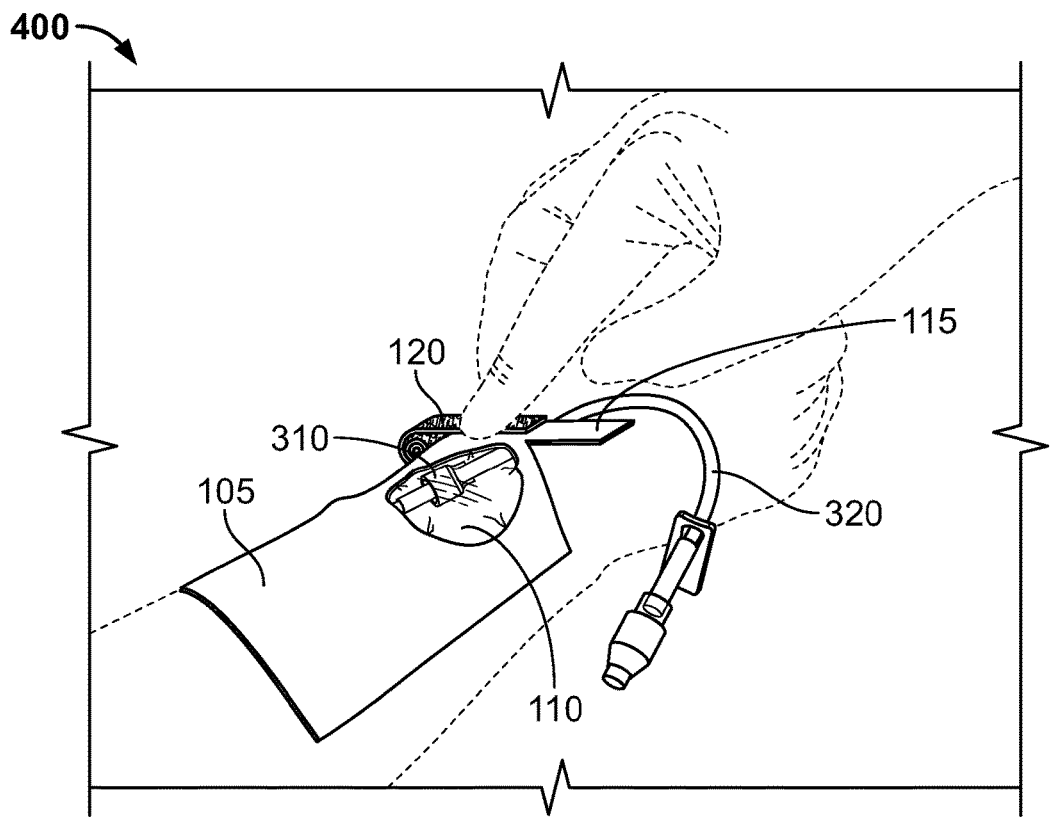
FIGS. 4-9 depict perspective views of an exemplary process of assembling the anchor system of FIG. 1 to the IV line of FIG. 3.

FIGS. 4-9 depict perspective views of an exemplary process of assembling the anchor system of FIG. 1 to the IV line of FIG. 3. FIG. 4 shows a perspective view of a step 400 of securing the IV line as shown in FIG. 3 against a portion of a patient's body (e.g., arm, leg, torso) using the first sheet of material 105 of the system 100 of FIG. 1. In an exemplary step, with the IV tubing 320 in place, the first sheet of material 105 is positioned around the injection site and the junction 310 to secure the IV line against the body. In this example, the first sheet of material 105 is positioned such that the window 110 surrounds the site of junction 310. The first sheet of material 105 provides a volume that may substantially protect the site of the junction 310 against ingress of contaminants or infection.

Figure 5A:
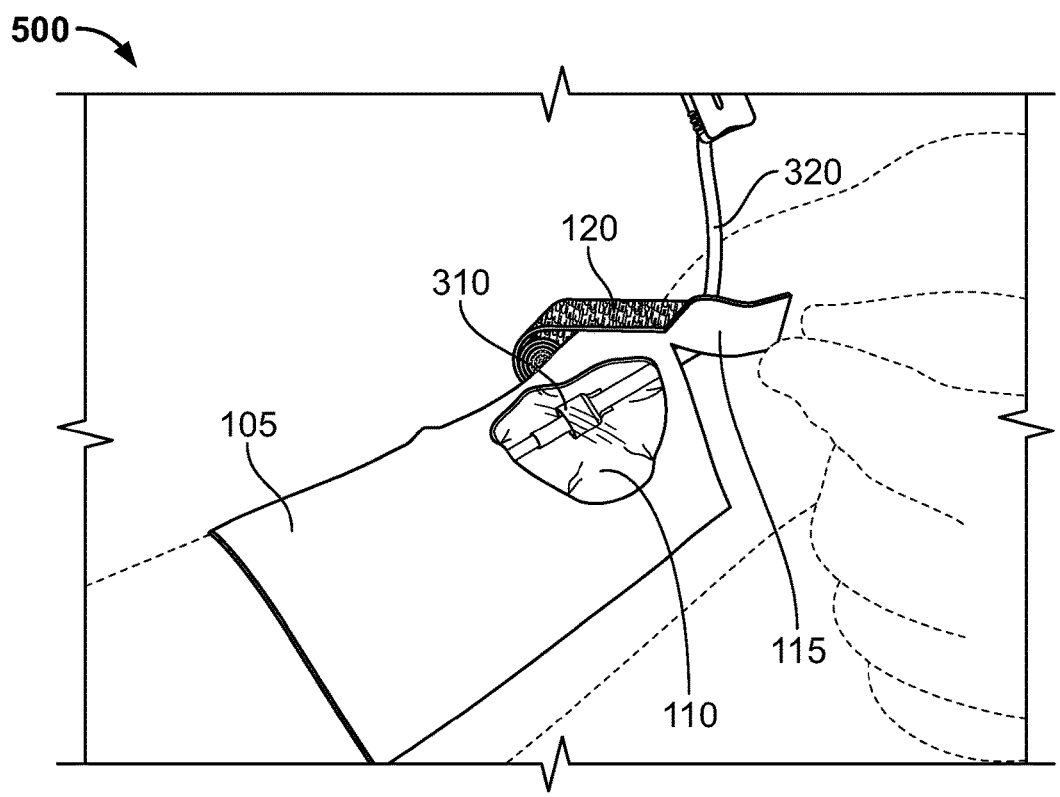
Figure 5B:
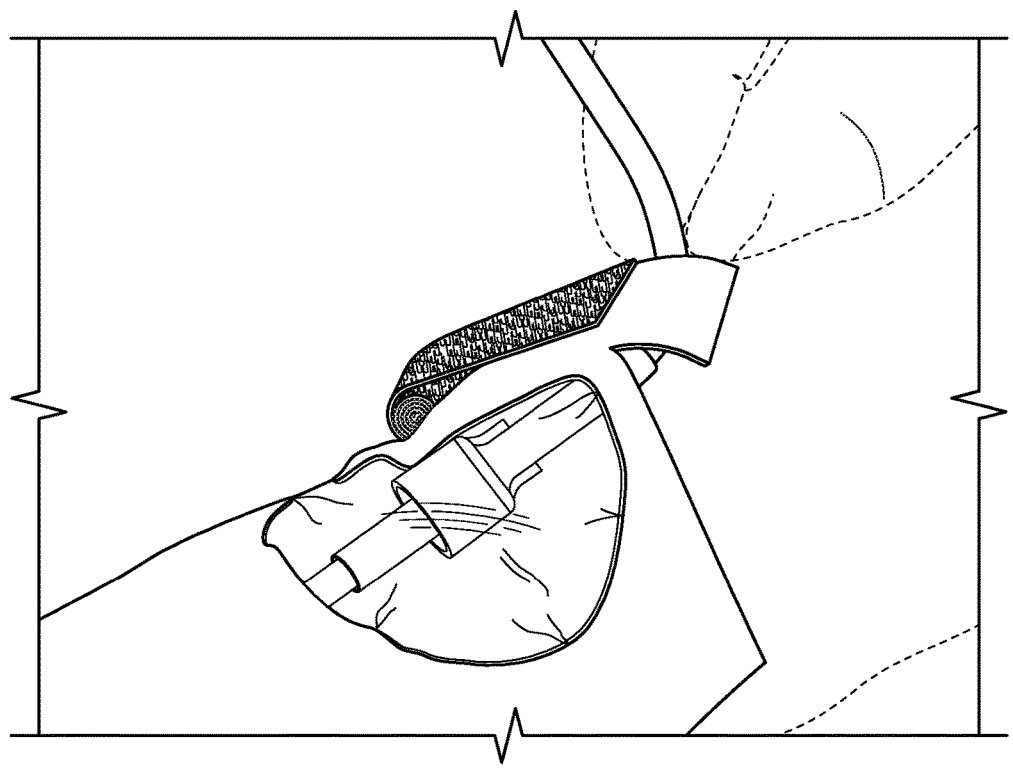
Figure 6:
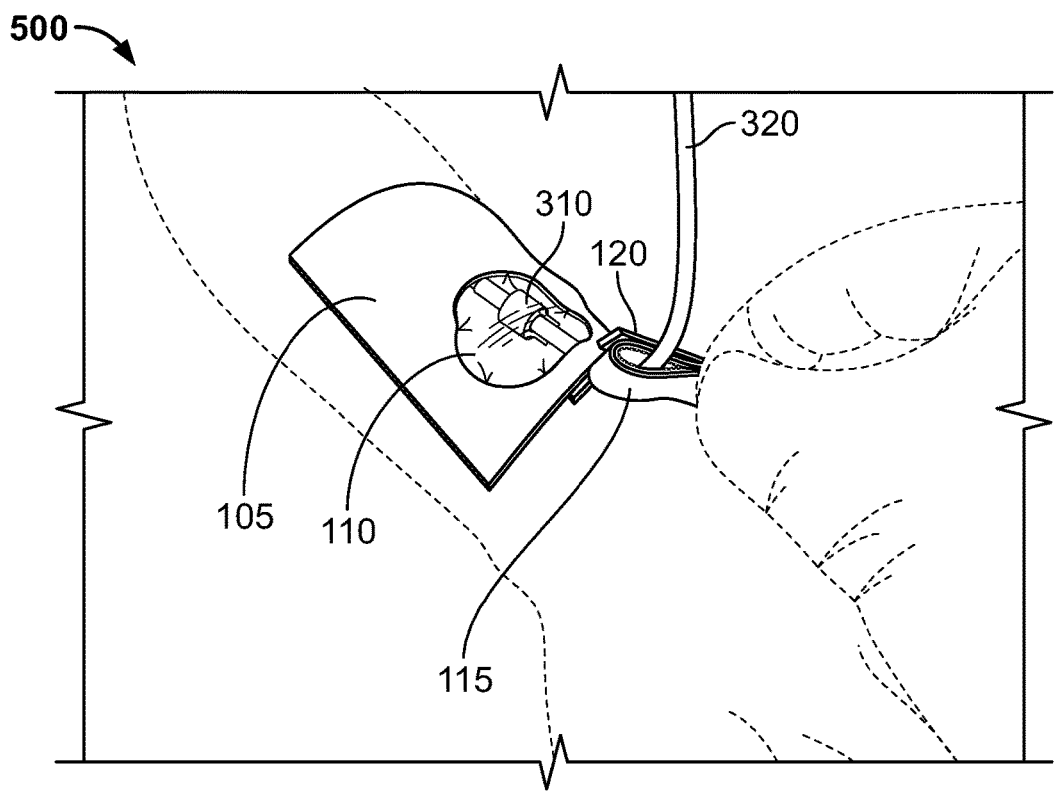
Figure 7:
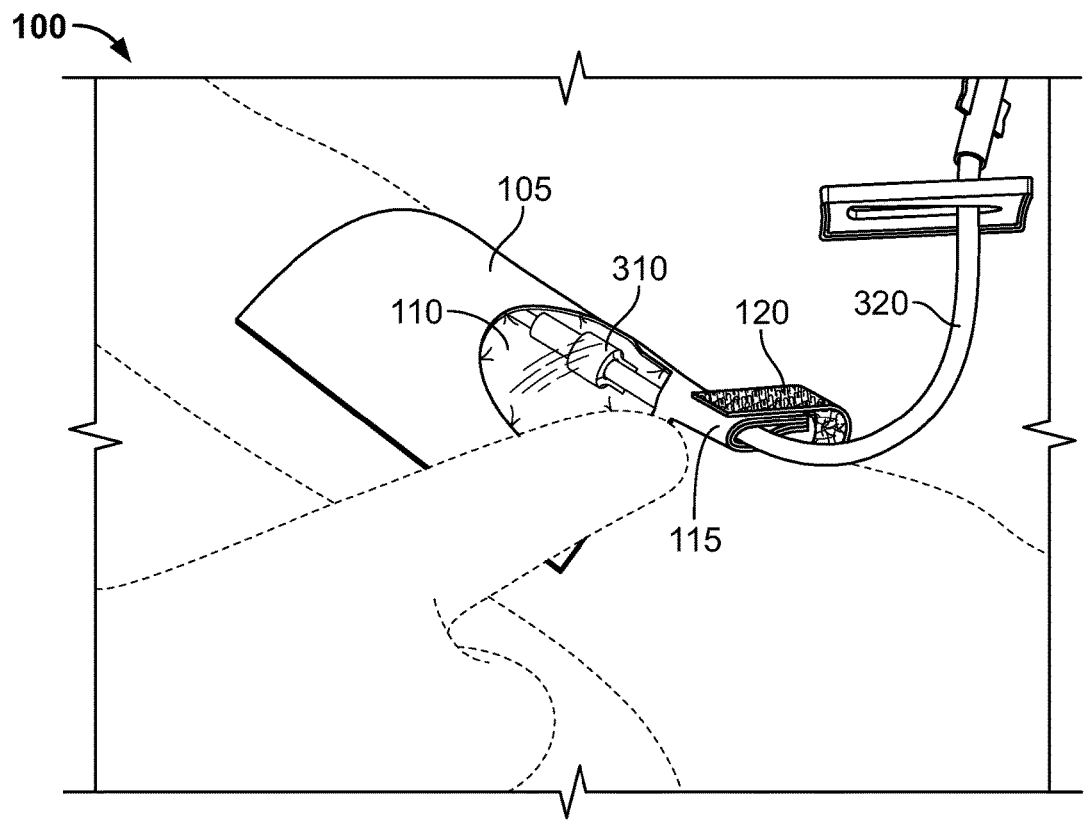

FIGS. 5-7 depict a perspective view of a step of securing the tubing relative to the catheter-and-hub assembly of the IV line as shown in FIG. 3 using the second sheet of material 115 of the anchor as shown in FIG. 1. In the depicted FIGS. 5-7 at step 500, the step may include using the second sheet 115 to secure a portion of the tubing 320 at the point of securement by the second sheet 115 against significant axial movement of the tubing relative to the catheter-and-hub assembly of the IV line. FIGS. 5-7 depict an exemplary progression of securing the second sheet 115 to the tubing. The second sheet of material 115 is secured around the tubing 320 with the opposing ends of the second sheet of material 115 secured to each other. In some implementations, the second sheet of material 115 may be adhesively coupled directly to the tubing alone or in conjunction with a secure coupling to itself. In some examples, the adhesive bond between the second sheet of material 115 and the tubing may be substantially permanent (e.g., not releasable). The second sheet of material 115 may advantageously locate the IV tubing 320 relative to the catheter-and-hub assembly to prevent disconnection of the tubing from the catheter-and-hub assembly.

Figure 8:
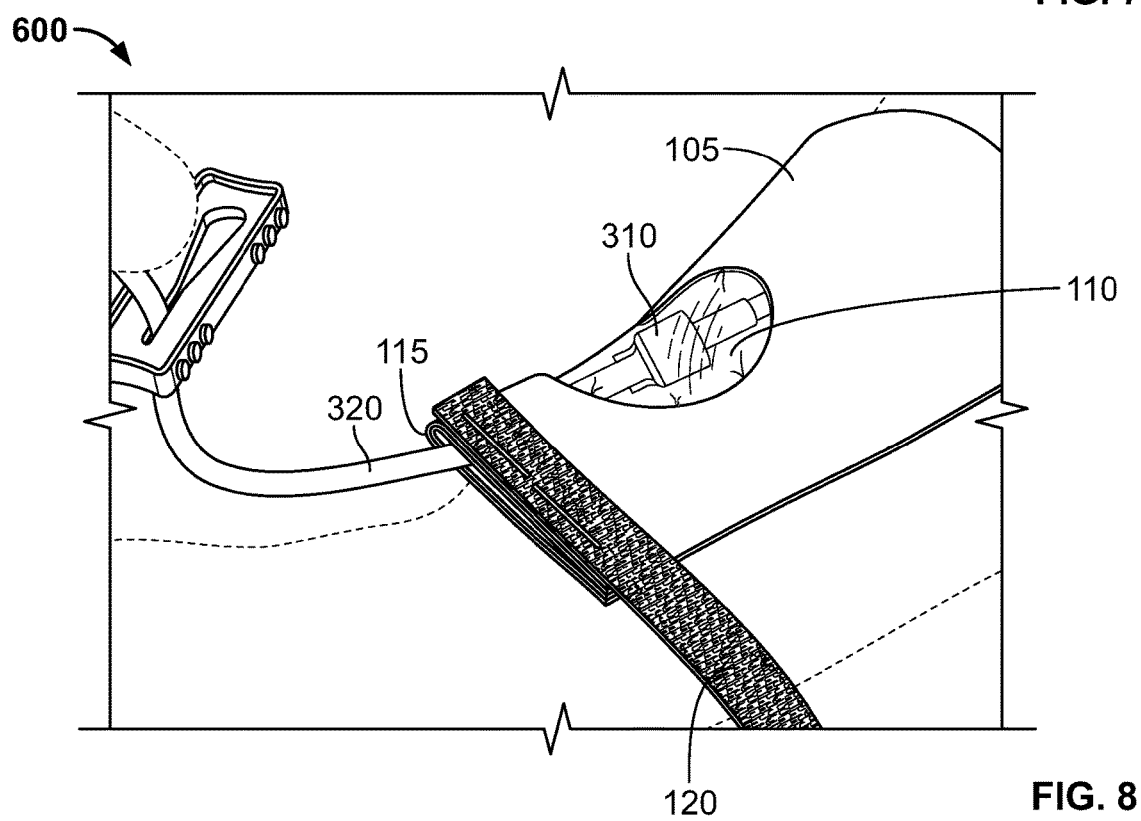
Figure 9:
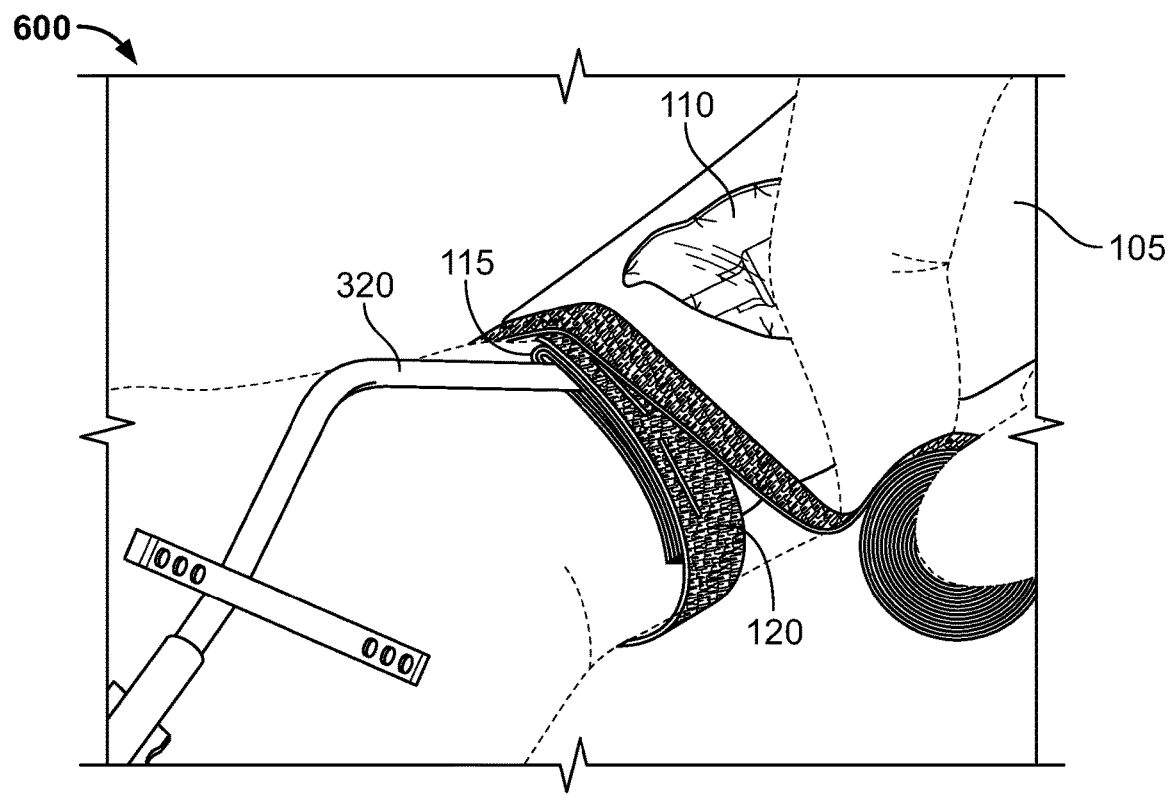

FIGS. 8 and 9 depict a perspective view of a step of securing the fastening device 120, as described with reference to FIG. 1, around a patient's limb to secure the site of junction between the catheter-and-hub assembly and tubing. In the depicted FIGS. 8 and 9 at step 600, the step may include using the fastening device 120 to secure a portion of the tubing against significant radial movement of the tubing relative to the catheter-and-hub assembly of the IV tubing 320. FIGS. 8 and 9 show the progression of securing the fastening device 120. In the depicted examples, the fastening device 120 is positioned around the patient's limb and releasably attached to itself.

Figure 10:
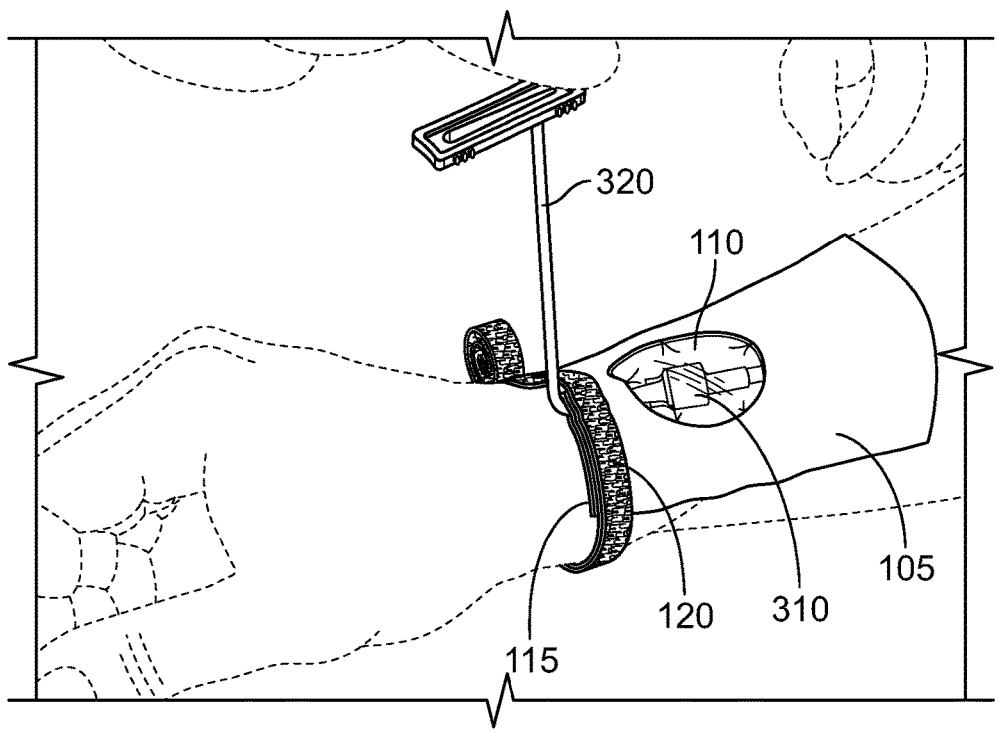
FIGS. 10 and 11 depict a perspective view of the anchor illustrating how the anchor provides strain relief to the IV line of FIG. 3.
Figure 11:
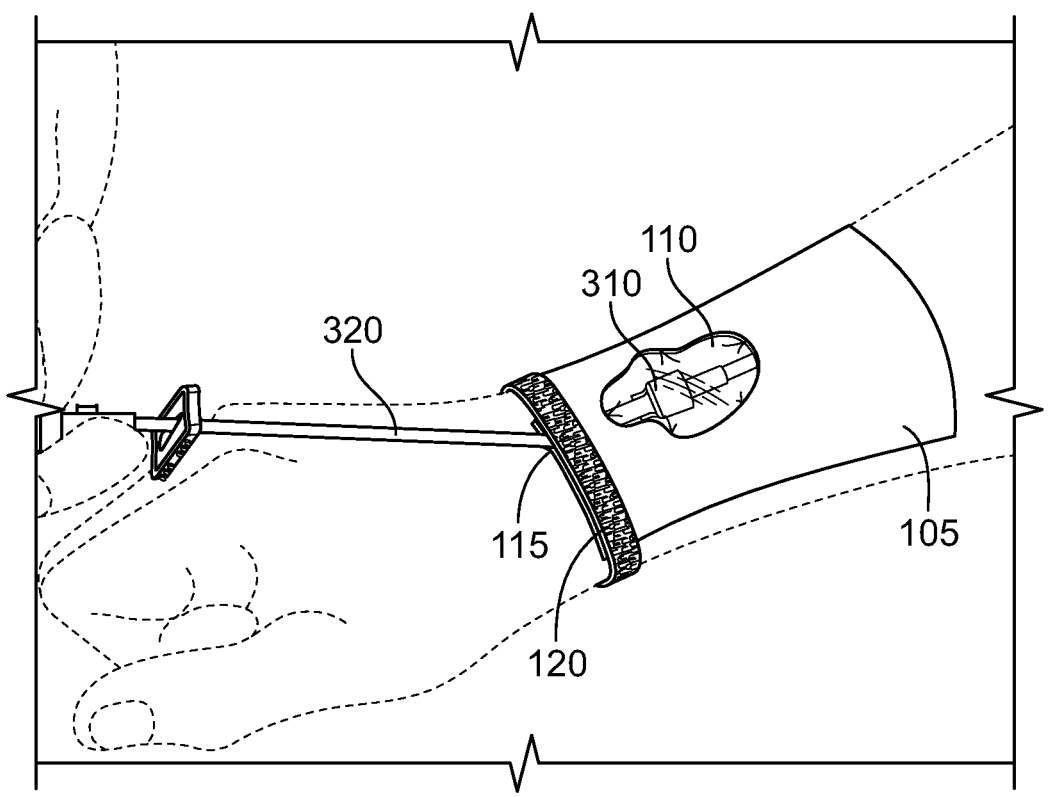

FIGS. 10 and 11 depict a perspective view of the exemplary anchor system illustrating how the anchor provides strain relief to the site of junction 310 between the tubing and the catheter-and-hub assembly. The anchor system 100 provides strain relief by absorbing forces exerted on the IV tubing 320 and preventing dislodging of the catheter out of the vein. In some embodiments the strain relief may also prevent disconnection of the catheter-and-hub assembly from the tubing 320.

FIG. 10 depicts a perspective view of the anchor adapted to absorb radial forces exerted on the IV line tubing 320. When the IV tubing 320 is pulled radially relative to the patient's limb, the fastening device 120 absorbs the radial pulling force and reduces the radial pulling force on the junction 310. Such radial strain relief may advantageously substantially mitigate or prevent dislodging of the catheter out the vein. In some embodiments, the strain relief also prevents disconnection of the tubing from the catheter-and-hub assembly (e.g., due to inadvertent snags on the tubing 320).

FIG. 11 depicts a perspective view of the anchor system 100 absorbing axial forces exerted on the IV line tubing 320. When the tubing is pulled axially relative to the patient's limb, the second sheet of material 115 may advantageously absorb substantially all axial pulling forces (e.g., up to a stiction force threshold depending on material interfaces and applied pressure). Such axial strain relief may advantageously mitigate and/or substantially prevent axial pulling force on the junction 310 to prevent dislodging of the catheter from the vein. Accordingly, embodiments of the anchor system 100 may advantageously reduce incidences of disconnection of the tubing from the catheter-and-hub assembly, and/or undesirable forces (e.g., torques) on the injection site itself, which could lead to injury of the patient or fault in the intravenous connection, for example.

Although various embodiments have been described with reference to the Figures, other embodiments are possible. For example, with reference to FIG. 1, the first sheet of material 105 may be a dressing adapted to cover an injection site into a portion of a patient's body for an intravenous assembly that provides fluid communication between the injection site and a fluid reservoir remote from the injection site through a length of flexible tubing. The second sheet of material 115 and the fastening device 120 may be adapted to cooperate to substantially absorb and/or relieve the strain at the injection site against forces on the tubing in any direction relative to the dressing sheet of material 105.

In an illustrative example, the second sheet of material 115 may be securely attached to the first sheet of material 105, and is flexibly adapted to wrap around IV tubing so as to resist axial or sliding movement of the tubing relative to the first sheet of material 105. The second sheet of material 115 is securely attached to the first sheet of material 105 at or near an edge of the first sheet of material 105, for example. The second sheet of material 115 may advantageously relieve the tubing against axial forces applied substantially parallel to the surface of the skin on the portion of the patient's body at a perimeter of the first sheet of material 105, such that the axial forces are attenuated at the injection site, by absorbing the axial forces. The second sheet of material 115 increases the axial forces required to disrupt or disconnect the injection site or the junction between catheter and hub.

In some embodiments, the second sheet of material 115 may include an adhesive to adhere the second sheet of material 115 to the tubing and opposing ends of the second sheet of material to tightly envelop and engage the tubing within the second sheet of material 115.

In an illustrative example, a portion of the second sheet of material 115 that directly contacts the tubing may be made, for example, from a material of high coefficient of friction. Examples of such materials may include, but are not limited to, rubber or flannel. In response to the pressure from the fastening device 120, the high coefficient of friction material may engage the surface of the tubing to substantially increase a static friction force or a threshold force along the axis of the tubing that would result in a sliding of the tube relative to the second sheet of material 120.

In some embodiments, the portion of the second sheet of material 115 that directly contacts the tubing may include an additional layer of material of high coefficient of friction to increase the friction between the second sheet of material and the tubing when they are in contact, such that the friction acts to grip the tubing within the first sheet of material.

In some implementations, the material with a high coefficient of friction may be textured to increase grip on the tubing to prevent sliding in response to axial forces. In some implementations, friction may substantially increase the force necessary to disrupt the injection site or junction or attenuates the force at the injection site or junction that is applied at the tubing.

Referring for example to FIG. 10, for example, the fastening device 120 may be secured to the first sheet of material 105 and adapted to wrap around the tubing 320 which is wrapped within the first sheet of material 105 against the portion of the patient's body so as to resist radial movement of the tubing relative to the first sheet of material 105. In some implementations, the fastening device 120 may advantageously substantially resist radial movement of the tubing relative to the body at the dressing sheet of material 105. By way of example, and not limitation, the fastening device 120 may be secured to the first sheet of material 105 near the edge where the first sheet of material 105 is connected with the second sheet of material 115. The fastening device 120 may substantially relieve the tubing against radial forces applied substantially perpendicular to the surface of the skin on the portion of the patient's body near a perimeter of the first sheet of material 105. The fastening device 120 may absorb at least a threshold amount of applied radial forces, such that the radial forces are attenuated at the injection site. The fastening device 120 may, in various implementations, substantially increase the radial forces required to disrupt or disconnect the injection site or the junction between catheter and hub. By wrapping around the first sheet of material 105 that encloses the tubing, the fastening device 120 also reinforces the strain relief of the tubing 320 from axial forces.

With reference to FIG. 6, the first sheet of material 115 may, in some examples, fold back onto itself around the tubing. In some implementations, after enclosing the tubing within the first sheet of material 115, the loose ends of the first sheet of material 115 may also be folded over the tubing or adhered to a patient's skin. With reference to FIG. 9, the fastening device 120 may be wrapped around a portion of the patient one or more times. The loose end may be releasably attached to the fastening device 120 itself. In some examples, the loose end of the fastening device 120 may be secured to the dressing sheet of material 105 and/or the first sheet of material 115.

In various embodiments, either or both of the first and second sheets of material 105, 115 and/or the fastening device 120 may be in various lengths or shapes, such as circular or elliptical, to accommodate different size patients, and/or different shape sites (e.g., torso, trunk, arms, leg, neck, wrist, hand, foot, head).

In some embodiments, the adhering ability of the first and second sheets of material 105, 115, or the fastening device 120 may be enhanced through attachment mechanisms in addition to or other than an adhesive. By way of example and not limitation, attachment mechanisms for securing may include devices such as a clamp, clip, or snap fastener, for example. In some embodiments, the adhesive may be exposed upon removal of a peel away release liner (e.g., backing). The second sheet 115 and the fastening device 120 may be configured for self-fastening, for example, the second sheet 115 and the fastening device 120 may each have one or more slits for mating with their loose ends. In some implementations, the loose end may be shaped for fastening with a slit. For example, a portion of the insertion end of the loose end may have an increased diameter to prevent disconnection with the slit. In some embodiments, the slit may be smaller than the insertion end of the loose end. In some implementations, the loose end may include a slit that cooperates with a slit on the respective second sheet 115 or fastening device 120.

The window 110 may be formed in some implementations as a resilient, breathable transparent plastic film. The window 110 may be an opening in the first sheet of material formed from a porous material to allow airflow into the site of connection between the catheter-and-hub assembly and tubing while still providing protection against contamination. In some examples, the window 110 may include a fabric material layer, which may be provided alone or in combination with another material such as an exterior breathable transparent plastic layer. The second sheet of material 115 may be formed by separation at perforations in the first sheet of material 105 or by being pre-cut from the first sheet of material 105. In some implementations, the sheets of material 105, 115 may be secured together by sewing, for example. The first sheet of material 105, second sheet of material 115, and the fastening device 120 may be formed from separate components and attached together. In some implementations, the second sheet of material 115 and the fastening device 120 may each be formed from different materials and attached at the perimeter of the first sheet of material 105 by various attachment means including but not limited to sewing, adhering, or stapling. In some implementations, the second sheet of material 115 and the fastening device 120 are attached onto the surface of the first sheet of material 105. A partial cut may be made along the perimeter of the second sheet of material 115 and the fastening device 120 next to the first sheet of material so the second sheet of material 115 and the fastening device 120 remain attached to the first sheet of material 105. In some embodiments, the fastening device 120 may be attached to the second sheet of material 115. In some implementations, the second sheet of material 115 and the fastening device 120 may be formed from a single material to form a unitary strip and attached to the first sheet of material 105. One end of the unitary strip may act as the second sheet of material 115 that directly contacts the tubing, and the other end may act as the fastening device 120 that wraps around the portion of the patient's body back onto itself. In some examples, the end that acts as the fastening device 120 may be longer than the end that acts as the second sheet of material 115.

In some examples, the fastening device 120 may be formed from a hook and loop-type fastener, for example. In some examples, the fastening device may provide a secure attachment after wrapping around the patient's body part. By way of example and not limitation, the fastening device may include attachment means such as one or more clamps, clips, buttons inserted within a slit, snap buttons, adhesive, or snap fasteners, any of which may be used alone or in combination with each other and/or with hook and loop attachment features. A release liner or backing may be used to expose the adhesive on the fastening device. In some implementations, the fastening device 120 may be secured to either or both of the sheets of material 105, 115 by sewing or stapling, for example. In some embodiments, the fastening device may be a mechanical fastener (e.g., rivet, staple).

In some embodiments, one or both of the second sheet of material 115 and/or fastening device 120 may be integrally formed with the dressing first sheet of material 105. For example, a cut may be made along the perimeter of one side of the first sheet of material 105 from opposing ends of the sides, leaving an intermediate portion intact. In another example, markings or perforations may be made to guide the tearing of the second sheet of material 115 and the fastening device 120 from the first sheet of material 105. In some implementations, the first sheet of material 105 may be pre-formed into a shape that allows for the fastening device 120 to be longer than the second sheet of material 115.

In some examples, the system 100 may be configured to manage and organize the components of the IV line by retaining each component at certain positions relative to other components. In some embodiments, the junction may form a connection between the catheter-and-hub assembly with either a saline cap, IV tubing extension set, or full IV tubing.

In some embodiments, a multiple attachment mechanisms could be integrated into a single strip. In some implementations, two or more second sheets of material 115 may be attached to the first sheet of material 105. Each of these second sheets of material 115 may wrap around the tubing. In some examples, one or both of these may directly contact the tubing, and one or both sheets may subsequently wrap around the body part in respectively opposite directions to provide further reinforcement. In some examples, these sheets may positioned substantially parallel and adjacent with one another and directly wrap around the tubing at different positions.

Although not meant to be in any way limiting, for purposes of simplifying explanation, the term "axial" forces as used with reference to an IV site on a limb (e.g., arm or leg) as depicted in the figures should be understood as referring to forces parallel to a central axis of an imaginary cylinder extending approximately along the length of the IV tubing around the point the tubing is anchored to the dressing. "Radial" forces should generally be understood as force components that are normal to this axis.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. A dressing for securing and protection of an intravenous (IV) assembly, the dressing comprising:
   a unitary body comprising:
     a longitudinally extending sheet (105) of non-rigid material comprising a window, wherein a first adhesive substance is disposed on a surface of the longitudinally extending sheet; and,
     a laterally extending tab (115) of non-rigid material extending from, and integrally formed with, the longitudinally extending sheet, wherein a second adhesive substance is disposed on a surface of the laterally extending tab, and the laterally extending tab is disposed at a distal end of the unitary body; and,
   a laterally extending fastening strip (120) of non-rigid material fixedly coupled to the unitary body, disposed at the distal end of the unitary body, and aligned with the laterally extending tab along a common lateral axis, such that the laterally extending tab and the laterally extending fastening strip extend laterally away from one another,
   wherein, in use, the dressing is configured such that:
     the first adhesive substance adhesively couples the longitudinally extending sheet to a skin surface of a patient to at least partially cover an injection site into a portion of a body part of the patient,
     the laterally extending tab wraps around an IV tube such that the laterally extending tab substantially separates the IV tube from the skin surface, and the second adhesive substance adhesively couples the laterally extending tab to the IV tube so as to resist axial movement of the IV tube relative to the body part of the patient, and,
     the laterally extending fastening strip wraps around the body part of the patient to securingly couple at least a portion of the IV tube to the body part of the patient so as to resist radial movement of the IV tube relative to the body part of the patient, while,
     the IV assembly and injection site are at least partially externally visible through the window.

2. The dressing of claim 1, wherein the window is formed of a transparent breathable film.

3. The dressing of claim 1, wherein at least one of the first adhesive substance and the second adhesive substance contain an antimicrobial agent.

4. The dressing of claim 1, wherein in operation, the dressing is further configured such that the laterally extending tab is adhesively attached to itself while being wrapped around the IV tube.

5. The dressing of claim 1, wherein in operation, the dressing is further configured such that the laterally extending fastening strip is releasably attached to itself.

6. The dressing of claim 1, wherein the laterally extending tab is hingedly coupled with the longitudinally extending sheet.

7. A dressing for securing and protection of an intravenous (IV) assembly, the dressing comprising:
   a unitary body comprising:
     a longitudinally extending sheet (105) of non-rigid material comprising a window, wherein a first adhesive means is disposed on a surface of the longitudinally extending sheet; and,
     a laterally extending tab (115) of non-rigid material extending from, and integrally formed with, the longitudinally extending sheet, wherein a second adhesive means is disposed on a surface of the laterally extending tab, and the laterally extending tab is disposed at a distal end of the unitary body; and,
   a laterally extending fastening strip (120) of non-rigid material fixedly coupled to the unitary body, disposed at the distal end of the unitary body, and aligned with the laterally extending tab along a common lateral axis, such that the laterally extending tab and the laterally extending fastening strip extend laterally away from one another,
   wherein, in use, the dressing is configured such that:
     the first adhesive means adhesively couples the longitudinally extending sheet to a skin surface of a patient to at least partially cover an injection site into a portion of a body part of the patient,
     the laterally extending tab wraps around an IV tube such that the laterally extending tab substantially separates the IV tube from the skin surface, and the second adhesive means adhesively couples the laterally extending tab to the IV tube so as to resist axial movement of the IV tube relative to the body part of the patient, and,
     the laterally extending fastening strip wraps around the body part of the patient to securingly couple at least a portion of the IV tube to the body part of the patient so as to resist radial movement of the IV tube relative to the body part of the patient, while, the IV assembly and injection site are at least partially externally visible through the window.

8. The dressing of claim 7, wherein at least one of the first adhesive means and the second adhesive means contain an antimicrobial agent.

9. The dressing of claim 7, wherein the laterally extending fastening strip comprises a hook and loop fastener.

10. The dressing of claim 7, wherein the laterally extending tab is hingedly coupled with the longitudinally extending sheet.

11. The dressing of claim 7, wherein:
the first adhesive comprises hydrogel, and,
in operation, the dressing is further configured such that the laterally extending fastening strip wraps around the body part of the patient at least once.

12. A dressing for securing and protection of an intravenous (IV) assembly, the dressing comprising:
a unitary body comprising:
a longitudinally extending sheet (105) of non-rigid material comprising a window, wherein a first adhesive substance is disposed on a surface of the longitudinally extending sheet, the first adhesive comprising hydrogel; and,
at least one laterally extending tab (115) of non-rigid material extending from, and integrally formed with, the longitudinally extending sheet, wherein a second adhesive substance is disposed on a surface of the at least one laterally extending tab, and the at least one laterally extending tab is disposed at a distal end of the unitary body; and,
wherein, in use, the dressing is configured such that:
the first adhesive substance adhesively couples the longitudinally extending sheet to a skin surface of a patient to at least partially cover an injection site into a portion of a body part of the patient, and,
the at least one laterally extending tab wraps around an IV tube such that the at least one laterally extending tab substantially separates the IV tube from the skin surface, and the second adhesive substance adhesively couples the at least one laterally extending tab to the IV tube so as to resist axial movement of the IV tube relative to the body part of the patient, while,
the IV assembly and injection site are at least partially externally visible through the window.

13. The dressing of claim 12, wherein the first adhesive comprises a hydrogel configured to adhesively couple the longitudinally extending sheet to the skin surface, the second adhesive is a different adhesive than the first adhesive, and the second adhesive is configured to substantially permanently couple the at least one laterally extending tab to the IV tube.

14. The dressing of claim 12, wherein the window is formed of transparent film.

15. The dressing of claim 12, wherein at least one of the first adhesive substance and the second adhesive substance contain an antimicrobial agent.

16. The dressing of claim 12, wherein in operation, the dressing is further configured such that the at least one laterally extending tab is adhesively attached to itself while being wrapped around the IV tube.

17. The dressing of claim 12, wherein the at least one laterally extending tab is hingedly coupled with the longitudinally extending sheet.

18. The dressing of claim 12, wherein in operation, the dressing is further configured such that the at least one laterally extending tab (115, 120) wraps around the body part of the patient at least once.

19. The dressing of claim 12, wherein the at least one laterally extending tab is formed by being pre-cut from the longitudinally extending sheet.

20. The dressing of claim 12, further comprising:
a laterally extending fastening strip (120) of non-rigid material fixedly coupled to the unitary sheet, disposed at the distal end of the unitary sheet, and aligned with the at least one laterally extending tab along a common lateral axis, such that the at least one laterally extending tab and the laterally extending fastening strip extend laterally away from one another,
wherein, in use, the dressing is further configured such that:
the laterally extending fastening strip wraps around the body part of the patient to securingly couple at least a portion of the IV tube to the body part of the patient so as to resist radial movement of the IV tube relative to the body part of the patient.

21. The dressing of claim 12, further comprising a unitary strip, wherein the unitary strip comprises the at least one laterally extending tab (115), and is also configured as a fastening device (120).

22. The dressing of claim 20, wherein:
the laterally extending fastening strip comprises a hook and loop fastener, and
in operation, the dressing is further configured such that the laterally extending fastening strip is releasably attached to itself.

* * * * *